United States Patent [19]

Gilbert

[11] 4,316,857

[45] Feb. 23, 1982

[54] DIMERIZATION PROCESS

[75] Inventor: Arthur H. Gilbert, Stockton-on-Tees, England

[73] Assignee: Imperial Chemical Industries Limited, London, England

[21] Appl. No.: 86,035

[22] Filed: Oct. 18, 1979

[30] Foreign Application Priority Data

Oct. 26, 1978 [GB] United Kingdom ............... 41989/78

[51] Int. Cl.³ .................... C07C 120/00; C07C 121/20
[52] U.S. Cl. ............................................. 260/465.8 D
[58] Field of Search ................................ 260/465.8 D

[56] References Cited

U.S. PATENT DOCUMENTS

| | | | |
|---|---|---|---|
| 4,059,542 | 11/1977 | Jennings et al. | 252/431 P |
| 4,089,890 | 5/1978 | Jennings et al. | 260/465.8 D |
| 4,100,186 | 7/1978 | Wright | 260/465.8 D |
| 4,102,915 | 7/1978 | Jennings et al. | 260/465.8 D |
| 4,126,632 | 11/1978 | Hogan et al. | 260/465.8 D |
| 4,129,587 | 12/1978 | Jennings et al. | 260/465.8 D |
| 4,129,589 | 12/1978 | Eliades et al. | 252/395 X |
| 4,138,428 | 2/1979 | Jennings et al. | 260/465.8 D |

OTHER PUBLICATIONS

Clark et al., Quarterly Reviews, 18, (1964), pp. 295–320.
Hackh's, Chemical Dictionary, 4th ed., (1969), Edited by Grant, McGraw-Hill, pp. 25 and 60.
Dietsche, Die Reaktion von Phosphinigsaureestern Mit Acrylnitril, Tetrahedron Letters, 51, pp. 6347–6351 (1966).

*Primary Examiner*—Joseph Paul Brust
*Attorney, Agent, or Firm*—Cushman, Darby & Cushman

[57] ABSTRACT

A process for the dimerization of acrylonitrile to dicyanobutene and methylene-glutaronitrile under the influence of a phosphinite or phosphonite catalyst uses as solvent a mixture of proton-donating organic solvent, an aromatic hydrocarbon solvent and an aliphatic hydrocarbon solvent in a specified ratio so facilitating product isolation by phase separation or liquid/liquid extraction.

12 Claims, No Drawings

DIMERIZATION PROCESS

The present invention relates to a dimerisation process and, in particular, to a process for the dimerisation of acrylonitrile to linear $C_6$ dinitriles.

In our copending British patent application No. 31148/78 we have described a group of novel organophosphorus compounds and their use as catalysts in the dimerisation of acrylonitrile. The novel compounds are phosphinites and phosphonites of general formula:

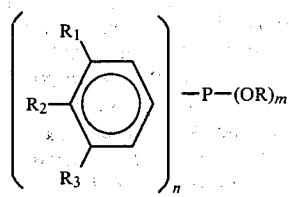

where $R_2$ is an electron-donating substituent, $R_1$ and $R_3$ are electron-donating substituents or hydrogen atoms, provided that they are not both hydrogen atoms, or either $R_1$ or $R_3$ forms part of a fused alicyclic ring with $R_2$, R is alkyl or cycloalkyl, and n and m are integers, each being either 1 or 2, provided that (m+n) equals 3, and when n is 2, the substituents on each aromatic ring may be the same or different.

By "electron-donating substituent" we mean a substituent of the aromatic nucleus which gives rise to a negative Hammett $\sigma$ constant.

A discussion on Hammett $\sigma$ constants and a table showing values for most common substituents is to be found in an article by Clark and Perrin in Quarterly Reviews, vol. 18, 1964 pp. 295–320.

Examples of suitable substituents $R_1$, $R_2$ and $R_3$ include alkoxy groups, e.g. methoxy, ethoxy, i-propoxy and t-butoxy; alkyl groups, e.g. methyl, ethyl and propyl; and alkyl amino groups, e.g. dimethylamino and diethylamino. The alkoxy, alkyl and alkylamino groups preferably contain from 1 to 8 carbon atoms, especially from 1 to 5 carbon atoms. It is essential that the groups $R_1$, $R_2$ and $R_3$ should be those which do not react adversely with the components of the reaction system.

Suitable groups R include alkyl groups such as methyl, ethyl, isopropyl, neopentyl, 2-ethylhexyl; and cycloalkyl groups such as cyclohexyl.

There is no finite limit on the numbers of carbon atoms which group R may contain, but it will commonly contain from 1 to 10 carbon atoms. When two groups R are present, they may be the same or different; but, generally, they will be the same.

The compounds of the invention may be used as catalysts for the dimerisation of acrylonitrile by the process described and claimed in our copending UK Patent Applications Nos. 45324/75 and 52888/75 (published as German OLS No. 2,649,904) and British Pat. No. 1,547,431. It is noted that UK Patent Application Nos. 45324/75 and 52888/75 combined correspond to U.S. Pat. No. 4,126,632 and British Pat. No. 1,547,431 corresponds to U.S. Pat. No. 4,102,915.

In such a process the acrylonitrile, substantially free of water and acrylonitrile stabilisers of the phenolic type, e.g. hydroquinone, is contacted with the phosphinite or phosphonite catalyst, the acrylonitrile being dissolved in an inert organic solvent which is capable of donating protons.

By an "inert" solvent is meant one which is substantially unreactive with respect to addition to, or reaction with, the unsaturated linkage of the acrylonitrile or the products of the acrylonitrile dimerisation. Furthermore, the solvent must not react with the phosphorus compound or catalytic intermediates to form inactive phosphorus species at such a rate as to seriously impair the dimerisation reaction.

Preferably hydroxylic solvents, such as alcohols, are used, provided always that they do not react adversely with the phosphorus compound or any intermediates it may form with acrylonitrile. This may be readily established by experiment. Tertiary and secondary alcohols are preferred, for example, t-butylalcohol, 2-butanol and isopropanol.

The concentration of proton-donating solvent is generally in the range 5 to 50% by volume, calculated on the total volume of the reactants, but the optimum concentration will vary with the precise nature of the solvent and the catalyst compound. The molar concentration of proton-donating solvent will generally be greater than the molar concentration of the phosphorus (III) compound.

In order to reduce the amount of hexamer and/or other oligomers or polymers (hereafter referred collectively as polymeric by-products or merely polymers) which may be co-produced with the desired dimeric products, it is often desirable to add an inert, non-hydroxylic co-solvent to the reaction mixture used in out process. It will be apparent that the co-solvent must be dried to a level which maintains the overall anhydrous state of the system.

Suitable non-hydroxylic organic solvents include hydrocarbons, for example, hexane, cyclohexane, toluene, and petroleum ethers; ethers, for example, tetrahydrofuran, diethyl ether and di-isopropyl ether; and nitriles, for example, acetonitrile, propionitrile; and fluorobenzenes. The hydrocarbon co-solvents are generally preferred. We have now found that by careful choice of the co-solvent there is produced a system which provides economies in the operation of the process particularly in respect of product separation and catalyst recycle.

According to the present invention a process for the dimerisation of acrylonitrile comprises contacting the acrylonitrile with a phosphinite or phosphonite of general formula

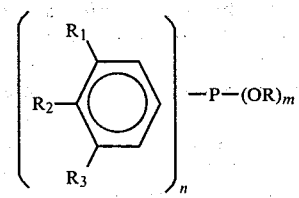

where $R_2$ is an electron-donating substituent, $R_1$ and $R_3$ are electron-donating substituents or hydrogen atoms, provided that they are not both hydrogen atoms, or either $R_1$ or $R_3$ forms part of a fused alicyclic ring with $R_2$, R is alkyl or cycloalkyl, and n and m are integers, each being either 1 or 2, provided that (m+n) equals 3, and when n is 2, the substituents on each aromatic ring may be the same or different, the acrylonitrile being present in solution in a mixed solvent comprising an inert organic solvent as hereinbefore described which is capable of donating protons and an inert hydrocarbon co-solvent which is a mixture of aromatic and aliphatic hydrocarbons, the nature of the components of the solvent mixture and their relative proportions being so chosen that the dicyanobutene and methyleneglutaronitrile products of the process separate from the solvent mixture or are separable therefrom by liquid/liquid extraction, the phosphinite or phosphonite catalyst remaining in the solvent mixture.

The ratio of aromatic hydrocarbon: aliphatic hydrocarbon: proton donating solvent: acrylonitrile is suitably in the range 3 to 7:3 to 7:0.5 to 1.5:3 preferably 5:5:1:3. In order that the dicyanobutene (DCB) and methyleneglutaronitrile (MGN) products of the process separate from the solvent mixture it is necessary for the conversion of the acrylonitrile to reach a certain figure. This figure is dependent upon the temperature of the reaction mixture e.g. in the case of the ratios preferred above at 60° C. separation of DCB and MGN will occur when the conversion of acrylonitrile is approximately 60%. If the reaction products are cooled prior to separation e.g. to 25° C. then the acrylonitrile conversion required for separation to take place can also be reduced. Alternatively, and preferably, the DCB and MGN may be removed from the reaction product by liquid/liquid extraction so that the catalyst remains in the solvent mixture which may, wholly or in part, be recycled. For the liquid/liquid extraction it is preferred to use an extractant boiling in the range 50° to 300° C. suitably a saturated nitrile e.g. adiponitrile, methylglutarodinitrile or ethylsuccindinitrile or mixtures of these three nitriles. Whichever method is used to remove the DCB and MGN the advantage of the present process over separating the reaction product by distillation includes the avoidance of catalyst damage caused by the heat of distillation as well as an energy saving.

The aromatic hydrocarbon solvent preferably boils in the range 75° to 150° C. and is suitably benzene or an alkylbenzene, preferably a methyl benzene e.g. toluene. The aliphatic hydrocarbon solvent may be an alkane or a cycloalkane and preferably boils in the range 30° to 150° C. Mixtures of aliphatic hydrocarbons may be used e.g. a mixture of alkanes boiling in the temperature range 40° to 80° C.

An essential feature of the present invention is that the reaction must be conducted in the substantial absence of water. Without prejudice to our invention, we believe that the water reacts with the catalyst in the presence of acrylonitrile to give non-catalytic addition compounds. Thus, the acrylonitrile, proton-donating solvent and co-solvents must be dried before use, otherwise the reaction may be completely inhibited. In particular acrylonitrile, which commonly contains as much as 4000 ppm of water, even after distillation, must be rigorously dried. It is also noted that hydroquinone stabilisers, which are present in acrylonitrile as supplied, should be removed. For example, if the reactants contain 300 ppm of water, reaction is seriously inhibited at a concentration of the phosphorus compound of 0.5% by volume, but at water concentrations of 50 ppm or lower reaction takes place readily. Any suitable drying technique may be used provided that the final water level is sufficiently low. For example, acrylonitrile and hydroxylic solvents may be dried by being contacted with calcium hydride or a 3A or 4A molecular sieve.

The concentration of the phosphorus compound in the reactant mixture may be varied over a wide range, for example, from 0.001, commonly 0.1, to 5% by volume, calculated on the volume of liquid reactants, but preferably the concentration is in the range 0.01 to 3% by volume.

The reaction temperature is commonly in the range 0° to 120° C., but it is generally preferred to keep the temperature below 75° C. to minimise polymerisation of the acrylonitrile and dimeric products. Preferably, the reaction temperature is in the range 20° to 70° C. It is noted that the reaction will proceed below 0° C., maintaining selectivity, but at a reduced rate.

Unlike other acrylonitrile dimerisation processes, the presence of compounds such as hydroquinone and its monomethyl ether, p-methoxyphenol, which are commonly used at present as acrylonitrile stabilisers, should be avoided.

The reaction may be carried out batchwise or continuously, the latter being preferred.

The invention will now be further described with reference to the following Examples in which all materials and apparatus were rigorously dried prior to use and all manipulations were carried out under moisture and oxygen free conditions (quantities are given in parts by weight).

EXAMPLE I

Acrylonitrile (24 parts), isopropanol (7.9 parts), toluene (43.3 parts), methylcyclohexane (38.5 parts) and isopropyl bis-3, 4-dimethylphenylphosphinite (1 part) were charged to a reaction vessel and heated at 60° C. After 3 hours reaction time, cooling to 15° C. caused separation into 2 phases. The upper phase (A) comprising the major proportion of solvents and catalyst was transferred to a second reaction vessel, make-up quantities of monomer and solvents added as necessary (to replace materials used in reaction and those removed with the product phase) (see Table 1) and then allowed to react further in a second cycle.

The lower phase was extracted twice by 30°–40° petroleum ether (15 parts and 6 parts) and the combined upper phases from this extraction transferred to a third reaction vessel. After evaporation of solvents this third reaction vessel, containing a small quantity of catalyst which had remained in the bottom phase from the first reaction vessel, was used to receive the upper phase (A) from the second reaction vessel and, after making up with monomer and solvents, (to replace materials used in reaction and those removed with the product phase) became the reaction vessel for the third cycle.

The lower phase from the petroleum ether extraction was analysed by GLC for 1,4 dicyanobutene and methyleneglutaronitrile after filtration to remove the hexamer.

Operation was continued in this way for 14 cycles, details of which are given in Table 1.

TABLE 1

| Charge: | Acrylonitrile (AN) 24 pts | Toluene 43.3 pts | Isopropyl bis 3, 4 |
| --- | --- | --- | --- |
| | Isopropanol (IPA) 7.9 pts | Methylcyclohexane 38.5 pts | dimethyl |
| | | | phenylphosphinite 1 pt |
| | MAKE-UP | REACTION TIME   TEMP | PRODUCTS |

TABLE 1-continued

| CYCLE | AN | IPA | TOLUENE | (hours) | (°C.) | 1,4 DCB | MGN | HEXAMER |
|---|---|---|---|---|---|---|---|---|
| 1 | — | — | — | 5.5 | 60 | 5.8 | 0.4 | 1.0 |
| 2 | 16 | 4 | — | 16 | 22 | 8.8 | 0.7 | 3.8 |
| 3 | 16 | 4 | — | 3.3 | 60 | 4.3 | 0.3 | 1.2 |
| 4 | 16 | — | — | 2.7 | 60 | 6.8 | 0.6 | 2.3 |
| 5 | 16 | — | — | 16 | 22 | 8.2 | 0.7 | 4.5 |
| 6 | 16 | 2 | — | 4 | 60 | 5.5 | 0.5 | 1.6 |
| 7 | 16 | 4 | 17 | 63 | 22 | 6.7 | 0.4 | 1.6 |
| 8 | 16 | 2 | — | 23 | 22 | 11.7 | 0.7 | 1.7 |
| 9 | 16 | 2 | — | 23.5 | 60 | 5.7 | 0.4 | 1.5 |
| 10 | 16 | 2 | — | 21.5 | 60 | 5.1 | 0.3 | 1.7 |
| 11 | 8 | 4 | — | 23.7 | 60 | 3.7 | 0.3 | 0.9 |
| 12 | 12 | 2 | — | 70.7 | 22 | 4.5 | 0.3 | 2.5 |
| 13 | 16 | 2 | — | 22.5 | 60 | 4.6 | 0.4 | 2.7 |
| 14 | 16 | 2 | 17 | 25.6 | 60 | 8.8 | 0.7 | 4.0 |

Average conversion of acrylonitrile over 14 cycles = 85%
DCB = dicyanobutene
MGN = methyleneglutaronitrile

EXAMPLE II

Acrylonitrile (20 parts), isopropanol (7.8 parts), toluene (43 parts), 30°-40° petroleum ether (33 parts) and isopropyl bis-3, 4-dimethylphenylphosphinite (0.2 parts) were charged to a reaction vessel and heated at 60° C. After 24 hours reaction time the reaction mixture was extracted twice with adiponitrile (10 parts and 5 parts respectively) and the upper phase comprising catalyst and a major part of the solvents transferred to a second reaction vessel.

The combined adiponitrile lower phases were then extracted twice by 30°-40° petroleum ether and the combined upper (petroleum ether) phase evacuated to remove most of the petroleum ether. The residue was then transferred to the second reaction vessel which after addition to make up quantities of monomer, solvent and catalyst became the reaction vessel for the second cycle.

The lower phase from the petroleum ether extraction was analysed as in Example I.

Operation was continued in this way for 4 cycles, details of which are given in Table 2.

$$\left[ \begin{pmatrix} R_1 \\ R_2 \bigcirc \\ R_3 \end{pmatrix}_n \right] - P - (OR)_m$$

where $R_2$ is an electron-donating substituent, $R_1$ and $R_3$ are electron-donating substituents or hydrogen atoms, provided that they are not both hydrogen atoms, or either $R_1$ or $R_3$ forms part of a fused alicyclic ring with $R_2$, R is either alkyl or cycloalkyl and n and m are intergers, each being 1 or 2, provided that (m+n) equals 3, and when n is 2, the substituents on each aromatic ring may be the same or different, the acrylonitrile being present in solution in a mixed solvent comprising an inert organic solvent which is capable of donating protons and an inert hydrocarbon co-solvent, the improvement whereby the inert hydrocarbon co-solvent is a mixture of a first hydrocarbon selected from the group

TABLE 2

| Charge: | | Acrylonitrile 20 pts Isopropanol 7.8 pts | | | Toluene 43 pts Petroleum Ether 33 pts | | Isopropyl bis-3, 4-dimethyl phenylphosphinite 0.2 pts | | |
|---|---|---|---|---|---|---|---|---|---|
| | | MAKE-UP | | | REACTION TIME | TEMP | PRODUCTS | | |
| CYCLE | AN | IPA | TOLUENE | PETROL | CAT | (hours) | (°C.) | 1, 4-DCB | MGN | HEXAMER | OTHERS |
| 1 | — | — | — | — | — | 26 | 60 | 8.3 | 0.7 | 0.5 | 0.4 |
| 2 | 16 | 2.8 | 9.9 | — | .025 | 22 | 60 | 7.1 | 0.6 | 0.5 | 0.4 |
| 3 | 15.5 | 3.5 | 8.7 | — | .021 | 22 | 60 | 6.9 | 0.6 | 0.4 | 1.1 |
| 4 | 15.5 | 3.9 | 12.1 | 2 | .026 | 22 | 60 | 5.8 | 0.6 | 0.2 | 0.5 |

Average conversion of acrylonitrile over 4 cycles = 63% consisting of benzene and alkylbenzenes boiling in the range between about 75° to 150° C. and a second hydrocarbon boiling in the range between about 30° to 150° C. selected from the group consisting of alkanes and cycloalkanes, so that the dicyanobutene product of the process separates from the solvent mixture or is separated therefrom by liquid/liquid extraction, the phosphinite or phosphonite catalyst remaining in the solvent mixture.

2. The process of claim 1 in which the ratio of first hydrocarbon:second hydrocarbon:proton donating solvent:acrylonitrile is in the range 3 to 7:3 to 7:0.5 to 1.5:3.

3. The process of claim 1 in which the dicyanobutene is separated from the catalyst and the solvent by extrac-

I claim:

1. In a process for the dimerisation of acrylonitrile to dicyanobutene which comprises contacting the acrylonitrile at a reaction temperature of 0° to 120° C. in the substantial absence of water and phenolic acrylonitrile stabilisers with a phosphinite or phosphinite of general formula:

tion with an extractant boiling in the range 50° to 300° C.

4. The process of claim 1 in which the inert organic solvent capable of donating protons is a hydroxylic solvent.

5. The process of claim 1 in which in the formula for the phosphinite or phosphonite $R_1$, $R_2$ and $R_3$ are alkoxy, alkyl, or alkylamino.

6. The process of claim 1 in which in the formula for the phosphinite or phosphonite R contains 1 to 10 carbon atoms.

7. The process of claim 1 in which:
(a) in the formula for the phosphinite or phosphonite $R_1$, $R_2$ and $R_3$ are methoxy, ethoxy, iso-propoxy, t-butoxy, methyl, ethyl, propyl, dimethylamino or diethylamino and R is methyl, ethyl, isopropyl, neopentyl, 2-ethylhexyl or cyclohexyl;
(b) The inert organic solvent capable of donating protons is tert-butanol, 2-butanol or isopropanol;
(c) The first hydrocarbon co-solvent boils in the range 75° to 150° C. and is benzene or an alkylbenzene;
(d) the second hydrocarbon co-solvent boils in the range 30° to 150° C. and is an alkane, cycloalkane or a mixture of alkanes boiling in the range 40° to 80° C.;
(e) the ratio of first hydrocarbon:second hydrocarbon:proton donating solvent:acrylonitrile is about 5:5:1:3;
(f) the reaction temperature is 20° to 70° C.;
(g) the dicyanobutene is separated from the catalyst and the solvent mixture by liquid/liquid extraction with adiponitrile.

8. The process of claim 1 which, upon completion of the contacting of acrylonitrile with catalyst, further comprises extracting the solvent mixture with at least one extractant selected from the group consisting of adiponitrile, methylglutarodinitrile, ethylsuccindinitrile and mixtures of these nitriles.

9. A process for the dimerisation of acrylonitrile to form a reaction product comprising dicyanobutene, said process comprising the steps of:
(a) contacting said acrylonitrile at a reaction temperature of 0° to 120° C. in the substantial absence of water and phenolic acrylonitrile stabilizers with a phosphinite or phosphonite catalyst of general formula:

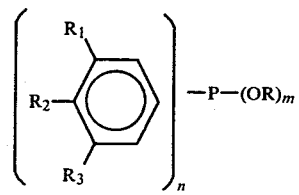

where $R_2$ is an electron-donating substituent, $R_1$ and $R_3$ are electron-donating substituents or hydrogen atoms, provided that they are not both hydrogen atoms, or either $R_1$ or $R_3$ forms part of a fused alicyclic ring with $R_2$, R is either alkyl or cycloalkyl and n and m are integers, each being 1 or 2, provided that (m+n) equals 3, and when n is 2, the substituents on each aromatic ring may be he same or different, the acrylonitrile being present in solution in a mixed solvent comprising an inert organic solvent which is capable of donating protons and an inert hydrocarbon co-solvent, the inert hydrocarbon co-solvent being a mixture of a first hydrocarbon selected from the group consisting of benzene and alkylbenzenes boiling in the range between about 75° to 150° C. and a second hydrocarbon boiling in the range between about 30° to 150° C. selected from the group consisting of alkanes and cycloalkanes, the nature of the components of the solvent mixture and their relative proportions being so chosen that the dicyanobutene product of the process is capable of separating from the solvent mixture;
(b) separating the reaction mixture of step (a) into two phases, the upper phase comprising said catalyst and said solvent mixture, and the lower phase comprising said dicyanobutene product;
(c) removing said upper phase from the separated reaction mixture of step (b); and
(d) recovering said product from said lower phase.

10. The process of claim 9 which further comprises the steps of:
(e) transferring said removed upper phase from step (c) to a reaction vessel;
(f) adding acrylonitrile to said reaction vessel of step (e);
(g) reacting acrylonitrile in said reaction vessel of step (e) to form a reaction mixture comprising dicyanobutene;
(h) separating the reaction mixture of step (g) into two phases, the upper phase comprising said catalyst and said solvent mixture, and the lower phase comprising said dicyanobutene product;
(i) removing said upper phase from the separated reaction mixture of step (h); and
(j) recovering said product from said lower phase of step (h), wherein said process is continuous.

11. The process of claim 10 wherein step (f) comprises: (I) adding make-up quantities of materials used in the reaction of said contacting step (a); and (II) adding make-up quantities of materials removed with the lower phase of step (b).

12. In a process for the dimerisation of acrylonitrile to dicyanobutene which comprises contacting the acrylonitrile at a reaction temperature of 0° to 120° C. in the substantial absence of water and phenolic acrylonitrile stabilisers with a phosphinite or phosphonite of general formula:

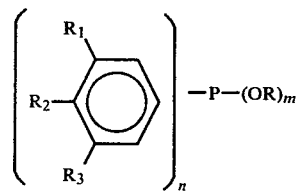

where $R_2$ is an electron-donating substituent selected from the group consisting of alkoxy, alkyl and alkylamino groups containing 1 to 8 carbon atoms, $R_1$ and $R_3$ are hydrogen atoms or electron-donating substituents selected from the group consisting of alkoxy, alkyl and alkylamino groups containing 1 to 8 carbon atoms provided that $R_1$ and $R_3$ are not both hydrogen atoms or either $R_1$ or $R_3$ forms part of a fused alicyclic ring with $R_2$, R is either an alkyl or cycloalkyl group containing from 1 to 10 carbon atoms and n and m are integers, each being 1 or 2, provided that (m+n) equals 3, and when n is 2 the substituents on each aromatic ring may be the same or different, the acrylonitrile being present in solution in a mixed solvent comprising an inert organic solvent which is capable of donating protons and an inert hydrocarbon co-solvent, the improvement whereby the inert hydrocarbon co-solvent is a mixture of a first hydrocarbon selected from the group consisting of benzene and alkylbenzenes boiling in the range 75° to 150° C. and a second hydrocarbon boiling in the range 30° to 150° C. selected from the group consisting of alkanes, and cycloalkanes and the dicyanobutene product of the process separation from the solvent mixture or is separated therefrom by liquid/liquid extraction, the phosphinite or phosphonite catalyst remaining in the solvent mixture.

* * * * *

UNITED STATES PATENT AND TRADEMARK OFFICE
CERTIFICATE OF CORRECTION

PATENT NO. : 4,316,857
DATED : February 23, 1982
INVENTOR(S) : Arthur H. Gilbert It is certified that error appears in the above—identified patent and that said Letters Patent is hereby corrected as shown below:

Column 5, line 67, change the second occurrence of "phosphinite" to -- phosphonite --.

Column 6, line 35, change "intergers" to -- integers --.

Signed and Sealed this

First Day of June 1982

[SEAL]

Attest:

Attesting Officer

GERALD J. MOSSINGHOFF

Commissioner of Patents and Trademarks